United States Patent [19]

Iwasaki et al.

[11] Patent Number: 5,179,081
[45] Date of Patent: Jan. 12, 1993

[54] METHOD OF TREATMENT USING AN ANTICOAGULANT POLYPEPTIDE

[75] Inventors: Akio Iwasaki, Matsudo; Makoto Suda, Tsukuba; Yushi Saino, Tokyo, all of Japan

[73] Assignee: Kowa Co., Ltd., Nagoya, Japan

[21] Appl. No.: 693,063

[22] Filed: May 1, 1991

Related U.S. Application Data

[63] Continuation of Ser. No. 379,266, Jul. 13, 1989, abandoned.

[30] Foreign Application Priority Data

Jul. 21, 1988 [JP] Japan .................. 63-182633

[51] Int. Cl.$^5$ ............................................. A61K 37/02
[52] U.S. Cl. ..................... 514/12; 530/350; 530/395; 435/69.2
[58] Field of Search ............ 514/12; 530/350, 395; 435/69.2

[56] References Cited

U.S. PATENT DOCUMENTS 4,873,222  10/1989  Arai ........................ 514/21

OTHER PUBLICATIONS

Crompton et al "Primary Structure of the human, membrane-associated $Ca^{2+}$ . . . "EMBO v. 7, No. 1 pp. 21-27 Jan. 1988.

*Primary Examiner*—David L. Lacey
*Assistant Examiner*—Nina Ossanna
*Attorney, Agent, or Firm*—Oblon, Spivak, McClelland, Maier & Neustadt

[57] ABSTRACT

A polypeptide having an amino acid sequence as shown in FIG. 1 and its preparation method are disclosed. A DNA fragment capable of coding CPBII polypeptide (human placenta-derived coagulation inhibitor) is first obtained from the human placental cDNA library by using a CPBII-specific antibody as a probe. Then, microorganism cells are transformed by the use of a recombinant plasmid incorporated with the DNA fragment, allowing the resultant transformant to express the CPBII gene, to finally obtain a CPBII-like polypeptide. The polypeptide of this invention exhibits strong anticoagulation activities, and useful for an active component of anticoagulation medicines and preventin in vivo blood coagulation.

7 Claims, 15 Drawing Sheets

X-Ala-Lys-Pro-Ala-Gln-Gly-Ala-Lys-Tyr-Arg-Gly-Ala-Ser-Ile-His-Asp-Phe-Pro-Gly-Phe-Asp
Pro-Asn-Gln-Asp-Ala-Glu-Ala-Leu-Tyr-Thr-Ala-Met-Lys-Gly-Phe-Gly-Ser-Asp-Lys-Glu
Ala-Ile-Leu-Asp-Ile-Ile-Thr-Ser-Arg-Ser-Asn-Arg-Gln-Arg-Gln-Glu-Val-Cys-Gln-Ser
Tyr-Lys-Ser-Leu-Tyr-Gly-Lys-Asp-Leu-Ile-Ala-Asp-Leu-Lys-Tyr-Glu-Leu-Thr-Gly-Lys
Phe-Glu-Arg-Leu-Ile-Val-Gly-Leu-Met-Arg-Pro-Pro-Ala-Tyr-Cys-Asp-Ala-Lys-Glu-Ile
Lys-Asp-Ala-Ile-Ser-Gly-Ile-Gly-Thr-Asp-Glu-Lys-Cys-Leu-Ile-Glu-Ile-Leu-Ala-Ser
Arg-Thr-Asn-Glu-Gln-Met-His-Gln-Leu-Val-Ala-Ala-Tyr-Lys-Asp-Ala-Tyr-Glu-Arg-Asp
Leu-Glu-Ala-Asp-Ile-Ile-Gly-Asp-Thr-Ser-Gly-His-Phe-Gln-Lys-Met-Leu-Val-Val-Leu
Leu-Gln-Gly-Thr-Arg-Glu-Glu-Ala-Gly-Glu-Asp-Val-Val-Ser-Gly-Thr-Asp-Glu-Gln-Asp-Val
Gln-Asp-Leu-Tyr-Glu-Ala-Gly-Glu-Glu-Lys-Gln-His-Leu-Arg-Leu-Val-Phe-Asp-Gly-Ala-Gln-Phe-Ile-Tyr
Ile-Leu-Gly-Asn-Arg-Ser-Lys-Gln-His-Leu-Arg-Leu-Val-Phe-Asp-Gly-Tyr-Leu-Lys-Thr
Thr-Gly-Lys-Pro-Ile-Glu-Ala-Val-Val-Lys-Cys-Ile-Arg-Gly-Glu-Leu-Ser-Gly-Asp-Phe-Glu-Lys-Leu
Met-Leu-Ala-Val-Val-Lys-Gly-Leu-Gly-Thr-Arg-Asp-Glu-Ala-Ser-Thr-Pro-Gly-Tyr-Phe-Ala-Glu-Arg-Leu-Phe
Lys-Ala-Met-Lys-Gly-Leu-Gly-Thr-Arg-Asp-Asn-Thr-Leu-Ile-Arg-Ile-Met-Val-Ser-Arg
Ser-Glu-Leu-Asp-Met-Leu-Asp-Ile-Arg-Glu-Ile-Phe-Arg-Thr-Lys-Gly-Lys-Ser-Leu
Tyr-Ser-Met-Ile-Lys-Asn-Asp-Thr-Ser-Gly-Glu-Tyr-Lys-Lys-Thr-Leu-Leu-Lys-Leu-Ser
Gly-Gly-Asp-Asp-Asp-Ala-Ala-Gly-Gln-Phe-Phe-Pro-Glu-Ala-Ala-Gln-Val-Ala-Tyr-Gln

*FIG. 1α*

Met-Trp-Glu-Leu-Ser-Ala-Val-Ala-Arg-Val-Glu-Leu-Lys-Gly-Thr-Val-Arg-Pro-Ala-Asn
Asp-Phe-Asn-Pro-Asp-Ala-Asp-Ala-Lys-Ala-Leu-Arg-Lys-Ala-Met-Lys-Gly-Leu-Gly-Thr
Asp-Glu-Asp-Thr-Ile-Ile-Asp-Ile-Thr-His-Arg-Ser-Asn-Val-Gln-Arg-Gln-Gln-Ile
Arg-Gln-Thr-Phe-Lys-Ser-His-Phe-Gly-Arg-Asp-Leu-Met-Thr-Asp-Leu-Lys-Ser-Glu-Ile
Ser-Gly-Asp-Leu-Ala-Arg-Leu-Ile-Leu-Gly-Leu-Met-Met-Pro-Pro-Ala-His-Tyr-Asp-Ala
Lys-Gln-Leu-Lys-Ala-Met-Glu-Gly-Ala-Gly-Thr-Asp-Glu-Lys-Ala-Leu-Ile-Glu-Ile
Leu-Ala-Thr-Arg-Thr-Asn-Ala-Glu-Ile-Arg-Ala-Ile-Asn-Glu-Ala-Tyr-Lys-Glu-Asp-Tyr
His-Lys-Ser-Leu-Glu-Asp-Ala-Leu-Ser-Ser-Gly-His-Phe-Arg-Arg-Ile-Leu
Ile-Ser-Leu-Ala-Thr-Gly-His-Arg-Glu-Glu-Gly-Gly-Glu-Asn-Leu-Asp-Gln-Ala-Arg-Glu
Asp-Ala-Gln-Val-Ala-Ala-Glu-Ile-Leu-Glu-Ile-Ala-Asp-Thr-Pro-Ser-Gly-Asp-Lys-Thr
Ser-Leu-Glu-Thr-Arg-Phe-Met-Thr-Ile-Leu-Cys-Thr-Arg-Ser-Tyr-Pro-His-Leu-Arg-Arg
Val-Phe-Gln-Glu-Phe-Ile-Lys-Met-Thr-Asn-Tyr-Asp-Val-Glu-His-Thr-Ile-Lys-Lys-Glu
Met-Ser-Gly-Asp-Val-Arg-Asp-Ala-Phe-Val-Ala-Ile-Val-Gln-Ser-Val-Lys-Asn-Lys-Pro
Leu-Phe-Phe-Ala-Asp-Lys-Leu-Tyr-Lys-Ser-Met-Lys-Gly-Ala-Gly-Thr-Asp-Glu-Lys-Thr
Leu-Thr-Arg-Ile-Met-Val-Ser-Arg-Ser-Glu-Ile-Asp-Leu-Leu-Asn-Ile-Arg-Arg-Glu-Phe
Ile-Glu-Lys-Tyr-Asp-Lys-Ser-Leu-His-Gln-Ala-Ile-Glu-Gly-Asp-Thr-Ser-Gly-Asp-Phe
Leu-Lys-Ala-Leu-Leu-Ala-Leu-Cys-Gly-Gly-Glu-Asp

*FIG. 1b*

```
GCCAAACCAG CACAGGGTGC CAAGTACCGG GGCTCCATCC ATGACTTCCC AGGCTTTGAC
CCCAACCAGG ATGCCGAGGC TCTGTACACT GCCATGAAGG GCTTTGGCAG TGACAAGGAG
GCCATATTGG ACATAATCAC CTCACGGAGC AACAGGCAGA GGCAGGAGGT CTGCCAGAGC
TACAAGTCCC TCTACGGCAA GGACCTCATT GCTGATTTAA AGTATGAATT GACGGGCAAG
TTTGAACGGT TGATTGTGGG CCTGATGAGG CCACCTGCCT ATTGTGATGC CAAAGAAATT
AAAGATGCCA TCTCGGGCAT TGGCACTGAT GAGAAGTGCC TCATTGAGAT CTTGGCTTCC
CGGACCAATG AGCAGATGCA CCAGCTGGTG GCAGCATACA AGATGCCTA CGAGCGGGAC
CTGGAGGCTG ACATCATCGG CGACACCTCT GGCCACTTCC AGAAGATGCT TGTGGTCCTG
CTCCAGGGAA CCAGGGAGGA GGATGACGTA GTGAGCGAGG ACCTGGTACA ACAGGATGTC
CAGGACCTAT ACGAGGCAGG GGAACTGAAA TGGGGAACAG ATGAAGCCCA GTTCATTTAC
ATCTTGGGAA ATCGCAGCAA GCAGCATCTT CGGTTGGTGT TCGATGAGTA TCTGAAGACC
ACAGGGAAGC CGATTGAAGC CAGCATCCGA GGGGAGCTGT CTGGGGACTT TGAGAAGCTA
ATGCTGGCCG TAGTGAAGTG TATCCGGAGC ACCCCGGAAT ATTTTGCTGA AAGGCTCTTC
AAGGCTATGA AGGGCCTGGG GACTCGGGAC AACACCCTGA TCCGCATCAT GGTCTCCCGT
AGTGAGTTGG ACATGCTCGA CATTCGGGAG ATCTTCCGGA CCAAGTATGA GAAGTCCCTC
TACAGCATGA TCAAGAATGA CACCTCTGGC GAGTACAAGA AGACTCTGCT GAAGCTGTCT
GGGGGAGATG ATGATGCTGC TGGCCAGTTC TTCCCGGAGG CAGCGCAGGT GGCCTATCAG
ATGTGGGAAC TTAGTGCAGT GGCCCGAGTA GAGCTGAAGG GAACTGTGCG CCCAGCCAAT
GACTTCAACC CTGACGCAGA TGCCAAAGCG CTGCGGAAAG CCATGAAGGG ACTCGGGACT
GACGAAGACA CAATCATCGA TATCATCACG CACCGCAGCA ATGTCCAGCG GCAGCAGATC
CGGCAGACCT TCAAGTCTCA CTTTGGCCGG GACTTAATGA CTGACCTGAA GTCTGAGATC
TCTGGAGACC TGGCAAGGCT GATTCTGGGG CTCATGATGC CACCGGCCCA TTACGATGCC
AAGCAGTTGA AGAAGGCCAT GGAGGGAGCC GGCACAGATG AAAAGGCTCT TATTGAAATC
CTGGCCACTC GGACCAATGC TGAAATCCGG GCCATCAATG AGGCCTATAA GGAGGACTAT
CACAAGTCCC TGGAGGATGC TCTGAGCTCA GACACATCTG CCACTTCAG GAGGATCCTC
```

FIG. 2a

```
ATTTCTCTGG CCACGGGGCA TCGTGAGGAG GGAGGAGAAA ACCTGGACCA GGCACGGGAA
GATGCCCAGG TGGCTGCTGA GATCTTGGAA ATAGCAGACA CACCCAGTGG AGACAAAACT
TCCTTGGAGA CACGTTTCAT GACGATCCTG TGTACCCGGA GCTATCCGCA CCTCCGGAGA
GTCTTCCAGG AGTTCATCAA GATGACCAAC TATGACGTGG AGCACACCAT CAAGAAGGAG
ATGTCTGGGG ATGTCAGGGA TGCATTTGTG GCCATTGTTC AAAGTGTCAA GAACAAGCCT
CTCTTCTTTG CCGACAAACT TTACAAATCC ATGAAGGGTG CTGGCACAGA TGAGAAGACT
CTGACCAGGA TCATGGTATC CCGCAGTGAG ATTGACCTGC TCAACATCCG GAGGGAATTC
ATTGAGAAAT ATGACAAGTC TCTCCACCAA GCCATTGAGG GTGACACCTC CGGAGACTTC
CTGAAGGCCT TGCTGGCTCT CTGTGGTGGT GAGGAC
```

*FIG. 2b*

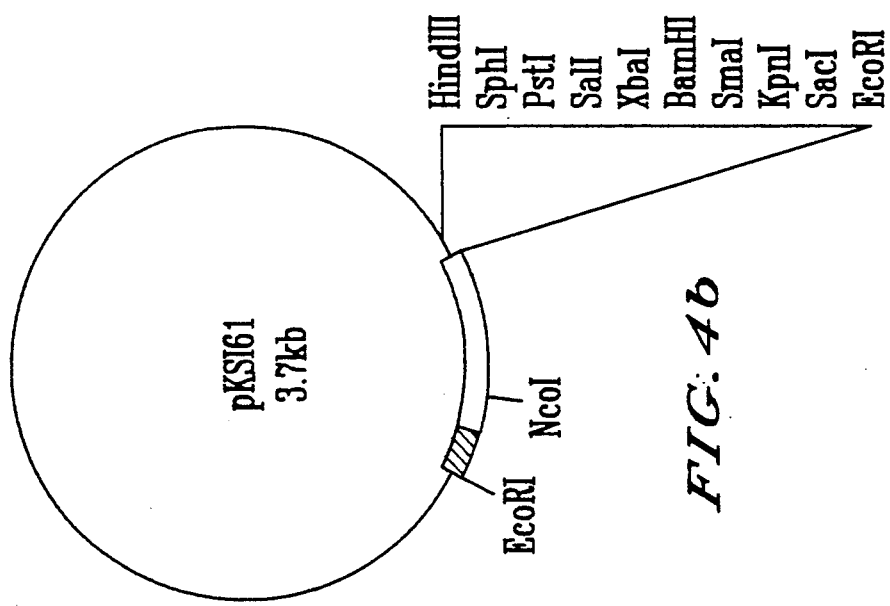
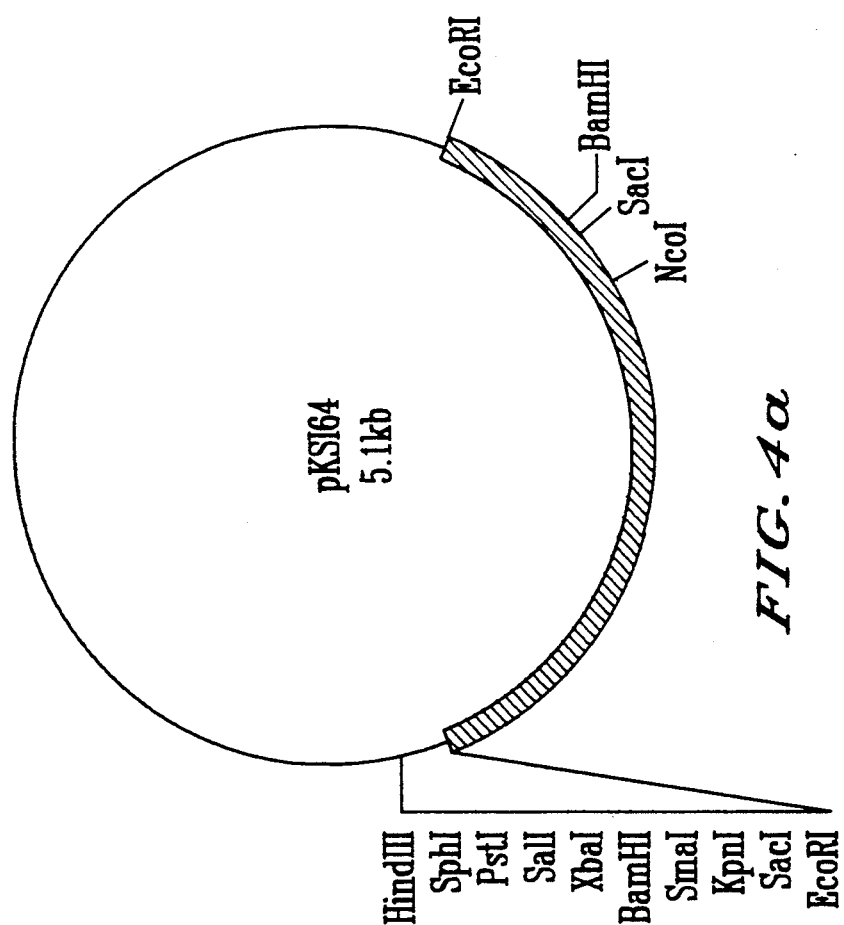

FIG. 5a

```
  1   ATG GCC AAA CCA GCA CAG GGT GCC AAG TAC CGG GGC TCC ATC CAT GAC TTC CCA GGC TTT GAC CCC AAC CAG GAT GCC GAG GCT CTG TAC   90
      Met Ala Lys Pro Ala Gln Gly Ala Lys Tyr Arg Gly Ser Ile His Asp Phe Pro Gly Phe Asp Pro Asn Gln Asp Ala Glu Ala Leu Tyr

ACT GCC ATG AAG AGG GGC TTT GGC AGT GAC AAG GAG ATA ATC ACC ATC TCA AGC AAC CGG AGC AGG CAG AGG GTC TGC CAG             180
      Thr Ala Met Lys Arg Gly Phe Gly Ser Asp Lys Glu Ile Ile Thr Ile Ser Ser Asn Arg Ser Arg Gln Arg Val Cys Gln

AGC TAC AAG TCC CTC TAC TAC GAA GAC CTC ATT GCT GAT TTA AAG TAT GAA TTG ACG GGC AAG TTT GAA CGG TTG ATT GTG GGC CTG ATG   270
      Ser Tyr Lys Ser Leu Tyr Tyr Glu Asp Leu Ile Ala Asp Leu Lys Tyr Glu Leu Thr Gly Lys Phe Glu Arg Leu Ile Val Gly Leu Met

AGG CCA CCT GCC TAT TGT GAT GCC AAA GAA ATT AAA GAT GCC ATC TCG ATT GGC ACT GAT GAG AAG TGC CTC ATT GAG ATC TTG GCT       360
      Arg Pro Pro Ala Tyr Cys Asp Ala Lys Glu Ile Lys Asp Ala Ile Ser Ile Gly Thr Asp Glu Lys Cys Leu Ile Glu Ile Leu Ala

TCC CGG ACC AAT GAG CAG ATG CAC CAG CTG GTG GCA GCA TAC AAA GAT GCC TAC GAG GAC CTG GAC CTG GCT GAC ATC ATC GGC GAC ACC   450
      Ser Arg Thr Asn Glu Gln Met His Gln Leu Val Ala Ala Tyr Lys Asp Ala Tyr Glu Asp Leu Asp Leu Ala Asp Ile Ile Gly Asp Thr

TCT GGC CAC TTC CAG AAG ATG CTT GTC GTC CTG CTC CAG GGA ACC AGG GAG GAT GAC GTA GTG AGC GAG GAC CTG GTA CAA CAG GAT       540
      Ser Gly His Phe Gln Lys Met Leu Val Val Leu Leu Gln Gly Thr Arg Glu Asp Asp Val Val Ser Glu Asp Leu Val Gln Gln Asp

GTC CAG GAC CTA TAC GAG GCA GGG GAA CTG AAA TGG GGA ACA GAT GAA GCC CAG TTC ATT TAC ATC TTG GGA AAT CGC AGC AAG CAG CAT   630
      Val Gln Asp Leu Tyr Glu Ala Gly Glu Leu Lys Trp Gly Thr Asp Glu Ala Gln Phe Ile Tyr Ile Leu Gly Asn Arg Ser Lys Gln His
```

```
640            650            660            670            680            690            700            710            720
CTT CGG TTG GTG TTC GAT GAG TAT CTG AAG ACC ACA GGG AAG CCG ATT GAA GCC AGC ATC CGA GGG GAG CTG TCT GGG GAC TTT GAG AAG
Leu Arg Leu Val Phe Asp Glu Tyr Leu Lys Thr Thr Gly Lys Pro Ile Glu Ala Ser Ile Arg Gly Glu Leu Ser Gly Asp Phe Glu Lys 730            740            750            760            770            780            790            800            810
CTA ATG CTG GCC GTA GTG AAG TGT ATC CGG AGC ACC CGG GAA TAT TTT GCT GAA AGG CTC TTC AAG GCT ATG AAG GGC CTG GGG ACT CGG
Leu Met Leu Ala Val Val Lys Cys Ile Arg Ser Thr Arg Glu Tyr Phe Ala Glu Arg Leu Phe Lys Ala Met Lys Gly Leu Gly Thr Arg 820            830            840            850            860            870            880            890            900
GAC AAC ACC CTG ATC CGC ATC ATG GTC TCC CGT AGT GAG TTG GAC ATG CTC GAC ATT CGG GAG ATC TTC CGG ACC AAG TAT GAG AAG TTT
Asp Asn Thr Leu Ile Arg Ile Met Val Ser Arg Ser Glu Leu Asp Met Leu Asp Ile Arg Glu Ile Phe Arg Thr Lys Tyr Glu Lys Ser 910            920            930            940            950            960            970            980            990
CTC TAC ATG ATC AAG AAT GAC ACC TCT GGC GAG TAC AAG ACT CTG AAG CTG TCT GGG GGA GAT GAT GCT GCT GCC CAG
Leu Tyr Met Ile Lys Asn Asp Thr Ser Gly Glu Tyr Lys Thr Leu Lys Leu Ser Gly Gly Asp Asp Ala Ala Gly Gln 1000           1010           1020           1030           1040           1050           1060           1070           1080
TTC TTC CCG GAG GCA GCG CAG GTG GCC TAT CAG ATG TGG GAA CTT AGT GAG GCA GTG GCC AAG GGA CTG AAG GGA ACT GTG CGC CCA GCC
Phe Phe Pro Glu Ala Ala Gln Val Ala Tyr Gln Met Trp Glu Leu Ser Glu Ala Val Ala Arg Gly Leu Lys Gly Thr Val Arg Pro Ala 1090           1100           1110           1120           1130           1140           1150           1160           1170
AAT GAC TTC AAC CCT GAC GCA GAT GCC AAA GCG CTG CGG AAG GGA CTC GAC GAA GAC ACA ATC ATC GAT ATC ATC
Asn Asp Phe Asn Pro Asp Ala Asp Ala Lys Ala Leu Arg Lys Gly Leu Asp Glu Asp Thr Ile Ile Asp Ile Ile 1180           1190           1200           1210           1220           1230           1240           1250           1260
ACG CAC CGC AGC AAT GTC CAG CAG ATC CGG CAG ACC TTC AAG TCT CAC TTT GGC CGG GAC TTA ATG ACT GAC CTG AAG TCT GAG
Thr His Arg Ser Asn Val Gln Gln Ile Arg Gln Thr Phe Lys Ser His Phe Gly Arg Asp Leu Met Thr Asp Leu Lys Ser Glu
```

```
     1270          1280          1290          1300          1310          1320          1330          1340          1350
ATC TCT GGA GAC CTG GCA AGG CTG ATT CTG GGG CTC ATG ATG CCA CAT TAC GAT GCC AAG AAG CAG TTG AAG AAG GCC ATG GAG GGA
Ile Ser Gly Asp Leu Ala Arg Leu Ile Leu Gly Leu Met Met Pro Ala His Tyr Asp Ala Lys Lys Gln Leu Lys Lys Ala Met Glu Gly 1360          1370          1380          1390          1400          1410          1420          1430          1440
GCC GGC ACA GAT GAA AAG GCT CTT ATT GAA ATC CTG GCC ACT CGG GCC ATC AAT GAG GCC TAT AAG GAG GAC
Ala Gly Thr Asp Glu Lys Ala Leu Ile Glu Ile Leu Ala Thr Arg Ala Ile Asn Glu Ala Tyr Lys Glu Asp 1450          1460          1470          1480          1490          1500          1510          1520          1530
TAT CAC AAG TCC CTG GAG GAT GCT CTG TCA GAC ACA TTC GGC AGG ATC CTC ATT TCT CTG GCC ACG GGG CAT CGT GAG
Tyr His Lys Ser Leu Glu Asp Ala Leu Ser Asp Thr Phe Gly Arg Ile Leu Ile Ser Leu Ala Thr Gly His Arg Glu 1540          1550          1560          1570          1580          1590          1600          1610          1620
GAG GGA GGA GAA AAC CTG GAC CAG CAG GCA GAT GCC CAG GTG GCT GCT GAG ATC TTG GAA ATA GCA GAC ACA CCC AGT GGA GAC AAA
Glu Gly Gly Glu Asn Leu Asp Gln Gln Ala Asp Ala Gln Val Ala Ala Glu Ile Leu Glu Ile Ala Asp Thr Pro Ser Gly Asp Lys 1630          1640          1650          1660          1670          1680          1690          1700          1710
ACT TCC TTG GAG ACA CGT TTC ATG ACG ATC CTG TGT ACC CGG AGC TAT CCG CAC CTC CGG AGA GTC TTC CAG GAG TTC ATC AAG ATG ACC
Thr Ser Leu Glu Thr Arg Phe Met Thr Ile Leu Cys Thr Arg Ser Tyr Pro His Leu Arg Arg Val Phe Gln Glu Phe Ile Lys Met Thr 1720          1730          1740          1750          1760          1770          1780          1790          1800
AAC TAT GAC GTG GAG CAC ACC ATC AAG AAG GAG ATG TCT GGG GAT GTC AGG GAT GCA TTT GTG GCC ATT GTT CAA AGT GTC AAG AAC AAG
Asn Tyr Asp Val Glu His Thr Ile Lys Lys Glu Met Ser Gly Asp Val Arg Asp Ala Phe Val Ala Ile Val Gln Ser Val Lys Asn Lys 1810          1820          1830          1840          1850          1860          1870          1880          1890
CCT CTC TTC TTT GCC GAC AAA CTT TAC AAA TCC ATG AAG GGT GCT ACA GAT GAG AAG ACT CTG ACC AGG ATC ATG TCC GTA CGC AGT
Pro Leu Phe Phe Ala Asp Lys Leu Tyr Lys Ser Met Lys Gly Ala Thr Asp Glu Lys Thr Leu Thr Arg Ile Met Val Ser Arg Ser
```

```
             1900            1910            1920            1930            1940            1950            1960            1970            1980
GAG ATT GAC CTG CTC AAC ATC CGG AGG GAA TTC ATT GAG AAA TAT GAC AAG TCT CTC CAC CAA GCC ATT CTC GAG GGT GAC ACC TCC GGA GAC
Glu Ile Asp Leu Leu Asn Ile Arg Arg Glu Phe Ile Glu Lys Tyr Asp Lys Ser Leu His Gln Ala Ile Glu Gly Asp Thr Ser Gly Asp
             1990            2000            2010            2020            2030            2040            2050            2060            2070            2080
TTC CTG AAG GCC TTG CTG GCT CTC TGT GGT GAG GAC TAGGGCCACAGCTTTGGGGCCACTTCTGCCAAGAAATGGTTATCAGCACCAGCTGCATGGCCAAG
Phe Leu Lys Ala Leu Leu Ala Leu Cys Gly Gly Glu Asp ***
     2090        2100        2110        2120        2130        2140        2150        2160        2170        2180        2190        2200
CCTGATTGTTCCAGCTCCAGAGACTAAGGAAGGGCAGGGGTGGGGGGAGGGGTTGGGCTCTTATCTTCAGTGAGCTTAGGAAGCTCCCACTCCCACGGGGCATCGAGGGC
     2210        2220        2230        2240        2250        2260        2270        2280        2290        2300        2310        2320
CCAGCACGGGCTGAGGGGCTGAAAAACGTAGCCATAGATCCTGTCCACCTCCACTCCCCTTGTCCACCCTCAGGCTTTCCCAGCTTCCTCCCCTTGCCAGCCTCTGCCCTGGTTTGGGC
     2330        2340        2350        2360
TATGTCAGATCCAAAAACATCCTGAACCTCTGTGTCTGT(A)
```

FIG.5d

AMIDE BLACK STAINING

1. E. coli JM105/pKSIX205 EXTRACT
    2. E. coli JM105/pKK223-3 EXTRACT

IMMUNO-STAINING

3. E. coli JM105/pKSIX205 EXTRACT
    4. E. coli JM105/pKK223-3 EXTRACT

METHOD OF TREATMENT USING AN ANTICOAGULANT POLYPEPTIDE

This application is a continuation of application Ser. No. 07/379,266, filed on Jul. 13, 1989.

BACKGROUND OF THE INVENTION i) Field of the Invention

This invention relates to a polypeptide having anticoagulant activities like a placental coagulation inhibitor (hereinafter called "CPBII") available from human tissues led by the human placenta, a novel DNA capable of coding the polypeptide, a recombinant plasmid containing the DNA, a transformant containing the recombinant plasmid, an anticoagulant containing the polypeptide as an effective ingredient and a process for the production of the polypeptide.

ii) Description of the Background Art

Heparin, heparin cofactor-II, antithrombin-III, $\alpha_2$-macroglobulin, $\alpha_1$-trypsin inhibitor, $C_1$-esterase inhibitor, protein C and the like have conventionally been known as anticoagulants. It is however only heparin that has found practical utility. Heparin however has a side effect of inducing bleeding tendency. Extremely stringent limitations are therefore imposed on its manner of administration and its dosage. Heparin has hence been not satisfactory as an anticoagulant from the standpoint of safety.

Under the aforementioned circumstances, the present inventors have already succeeded in separating and purifying CPBII from the human placenta, on which an application has been filed (Japanese Patent Application Laid-open No. 96132/1988).

CPBII is a substance which has the following properties and is useful as a medicine:
(1) Molecular weight (SDS-polyacrylamide gel electrophoresis, reduced state): $73,000 \pm 2,000$.
(2) Isoelectric point (isoelectric column electrophoresis using an ampholyte): 6.2–6.6.
(3) Stability:
   (a) Inactivated by a heat treatment at 50° C. for 30 minutes.
   (b) Stable in a pH range of 5.5–8.5 (37° C.).
   (c) Stable in plasma at 37° C. for 15 minutes.
(4) Action:
   (a) Capable of prolonging the recalcification time.
   (b) Capable of prolonging the prothrombin time.
   (c) Capable of prolonging the activated partial thromboplastin time.
(5) Analysis of amino acids:
   The existence of aspartic acid, threonine, serine, glutamic acid, proline, glycine, alanine, cystine, valine, methionine, isoleucine, leucine, tyrosine, phenylalanine, histidine, lysine and arginine is recognized by the analysis of amino acids.

The present inventors have also prepared a monoclonal antibody specific to CPBII and already filed an application for patent thereon (Japanese Patent Application No. 86753/1988). It is feasible to perform high-sensitivity assay, purification, etc. of the CPBII by using these monoclonal antibodies.

Several problems have however arisen because human tissues typified by human placentae are presently indispensable as a raw material for obtaining CPBII. For example, there is a limitation imposed on the quantity of CPBII available form a human tissue. Difficulties are always accompanied upon collection of human tissues as a raw material, whereby stable supply of the raw material is difficult. In addition, the potential danger of pathogenic viruses which may be contained in human tissues is not ignorable.

It has hence been desired to develop a method for supplying CPBII at a lower price, in a larger volume, more stably and more safely or to develop a substance having effects similar to CPBII.

SUMMARY OF THE INVENTION

The present inventors have proceeded with an extensive investigation with a view toward solving these problems. As a result, it has been found that a DNA fragment capable of coding the CPBII polypeptide can be obtained from the human placental cDNA library by using the CPBII-specific antibody as a probe, and a CPBII-like polypeptide can also be produced by transforming cells of a microorganism with a recombinant plasmid, in which the DNA fragment has been incorporated, and then allowing the resultant transformant to express the CPBII gene, leading to completion of the present invention.

BRIEF DESCRIPTION OF THE DRAWINGS

FIG. 1 shows an amino acid sequence of the polypeptide of this invention, where X denotes a methionine residue (Met), acetyl or a hydrogen atom.

FIG. 2 shows a nucleotide sequence of the cDNA of this invention.

FIG. 4 provides restriction endonuclease maps of the recombinant plasmids of this invention, pKSI 64 and pKSI 61.

FIGS. 5-1 and 5-2 show the whole nucletide sequence of cDNA of this invention and the amino acid sequence corresponding thereto.

DETAILED DESCRITPTION OF THE INVENTION AND PREFERRED EMBODIMENTS

Figure 3:
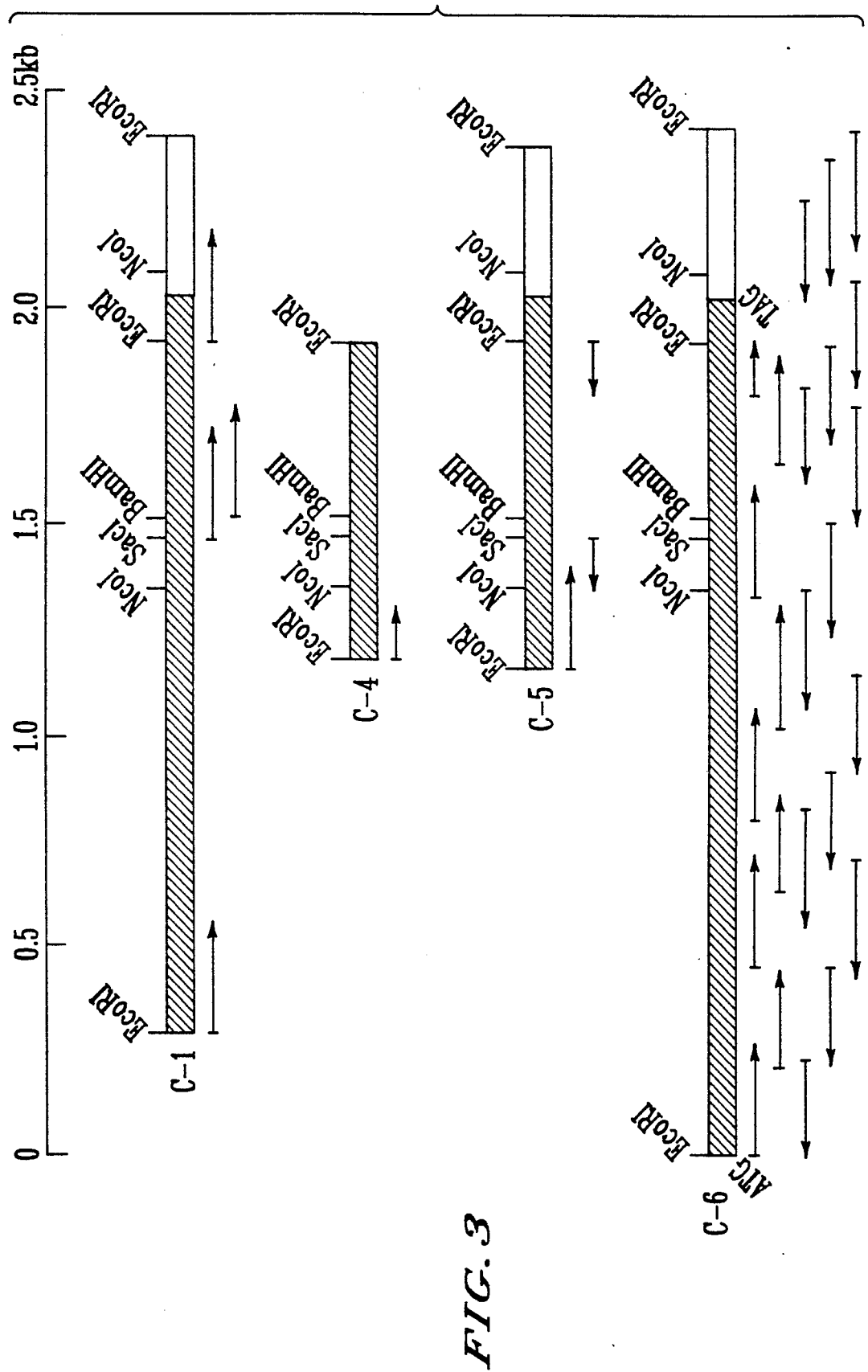
FIG. 3 provides restriction endonuclease maps of the cDNA insertion fragment of this invention.

The DNA coding the polypoptide of this invention, the recombinant plasmid and the transformant may be produced, for example, by the following steps:

(1) An antibody-positive clone is screened out from the human placenta cDNA library by using the CPBII-specific antibody. (2) The recombinant DNA is prepared from the antibody-positive clone thus isolated, and cDNA fragments are cut from the recombinant phage DNA by treating the later with a restriction endonuclease and are then incorporated into a plasmid vector. (3) Host cells are transformed with the resulting cDNA recombinant plasmid, thereby obtaining transformants of this invention. The thus-obtained transformants of this invention are cultured, whereby a recombinant plasmid of this invention which contains the DNA fragment of this invention is obtained from cells thus cultured. DNA fragments according to this invention may then be obtained by cleaving the thus-obtained recombinant plasmids with a suitable restriction endonuclease.

The above steps will next be described individually.

(1) Screening of the antibody-positive clone from the human placenta cDNA library:

The cDNA library may be prepared by preparing mRNA from a human placenta and then treating mRNA with a reverse transcriptase and a suitable vector DNA. Commercial cDNA library, for example, the human placental cDNA library (λgt11) produced by Clontech Laboratories, Inc. may also be used as an alternative.

The cDNA library prepared using λgt11 as a vector may be subjected to screening by using a particular antibody as a probe in accordance with a method proposed by Young and Davis [Huynh, T. V., Young, R. A. and Davis, R. W. (1985) In: *DNA Cloning*: A practical Approach, vol. 1, (D. M. Glover, ed.) pp 49–78, IRL Press, Oxford], so that a clone specific to the particular antibody may be isolated.

As primary antibodies useful as probes, may be mentioned CPBII-specific antibodies, e.g., anti-CPBII rabbit polyclonal antibody, anti-CPBII mouse polyclonal antibody and anti-CPBII monoclonal antibodies. Of these, anti-CPBII monoclonal antibodies, especially, anti-CPBII mouse monoclonal antibody is preferred. The antibody may be used in any form of serum, ascitic fluid, cell culture fluid and purified immunoglobulin.

The detection of a primary antibody conjugated with an antigen may be performed by autoradiography, which makes use of protein A labelled with radioactive iodine ($^{125}I$) or an anti-immunoglobulin antibody labelled with radioactive iodine ($^{125}I$), or by enzyme immunoassay in which an anti-immunoglobulin antibody labelled wilth a peroxidase or an anti-immunoglobulin antibody labelled with an alkaline phosphatase is used.

Incidentally, the anti-CPBII monoclonal antibody may be produced, for example, by the process reported by Köhler and Milstein (Nature, vol 256, pp. 495–497, 1975). According to this process, a mouse is immunized with CPBII which has been purified subsequent to its extraction from human placetae. Spleen cells are collected from the mouse and are then caused to undergo cell fusion with mouse myeloma cells. The cells, which have been subjected to the cell fusion, are cultured using an HAT selective medium, whereby hybridomas are alone allowed to multiply. Using CPBII as an antigen, the culture with the hybridomas thus multiplied is thereafter subjected to screening by enzyme immunoassay, thereby obtaining a hybridoma capable of producing a monoclonal antibody specific to CPBII. The monoclonal antibody is obtained from a culture in which the hybridoma thus obtained has been cultured or from the ascitic fluid of a mouse which has been inoculated the hybridoma.

(2) Preparation of CPBII cDNA recombinant plasmid:

Recombinant λgt11 phage DNA is extracted in a purified form from the thus-isolated antibody-positive clone in accordance with the method proposed by Young and Davis [Huynh, T. V., Young, R. A. and Davis, R. W. (1985) In: DNA Cloning: A Practical Approach, vol. 1 (D. M. Glover, ed.) pp 49–78, IRL Press, Oxford]. cDNA can be separated from the vector DNA by digesting the thus-purified recombinant λgt11 phage DNA with a restriction endonuclease EcoRI. The resultant cDNA is caused to rejoin with various cloning plasmid vectors which have been obtained by digestion with EcoRI, whereby recombinant plasmids are prepared. As usuable plasmid vectors, pBR322, pBR325, pUC18, pUC118, pTZ18R and the like may be mentioned.

(3) Transformation of host cells with the CPRII cDNA recombinant plasmid as well as preparation of recombinant plasmid of this invention and DNA of the present invention:

The resultant CPII cDNA recombinant plasmid is introduced into various host cells capable of using to the maximum extent the gene marker which the recombinant plasmid has, whereby the host cells are transformed. As host cells, *E. coli* is preferred. Various variants of *E. coli* K12 strain, for example, HB101, C600K, JM101, JM105, x1776, MV1304 and the like may be used. The competent cell method relying upon a calcium treatment or a like method may be used for the introduction of the recombinant plasmid.

The transformant is then cultured in a selective medium suitable for the gene marker of the vector plasmid and the recombinant plasmid of this invention is harvested from the cells.

Where pUC118 or pTZ18R is used as a vector, a single-stranded DNA can be prepared from the resultant transformant of *E. coli*, which contains the recombinant vector by infecting with a helper phage M13K07. The nucleotide sequence of the resultant single-stranded DNA can be determined by the dideoxynucleotide chain termination method [Sanger, F., Nicklen, S. and Coulson, A. R.: DNA Sequencing with Chain Terminating Inhibitors, Proc. Natl. Aca. Sci. USA, 74, 5463–5467 (1977)].

In the above nucleotide sequence, the nucleotide sequence of the part coding the polypeptide, one of intended substances in the present invention, may be illustrated in FIG. 2.

The DNA fragment of this invention is not necessarily limited to the above nucleotide sequence so long as it has ability to code the amino acid sequence described above. The recombinant plasmid of this invention may result from ligation with any vector DNA derived from *E. coli, B. subtilis*, yeast, mammal viruses or the like, provided that the recombinant plasmid of this invention has a nucleotide sequence capable of coding the above-described amino acid sequence and is replicative.

The polypeptide according to this invention can be produced by culturing a transformant containing the recombinant plasmid of this invention and harvesting the production of polypeptide of this invention, it is however necessary to construct a plasmid for expression of CPBII cDNA, which contains the following nucleotide sequences (1)–(6) in order in the downstream direction of transcription:

(1) a nucleotide sequence acting as a promoter, (2) a nucleotide sequence serving as a ribosome-binding site, (3) a nucleotide sequence serving as an initiation codon, (4) a nucleotide sequence capable of coding the amino acid sequence of the polypeptide of this invention, (5) a nucleotide sequence serving as a termination codon, and (6) a nucleotide sequence acting as a transcription terminator, and then to transform the host cells.

As a vector host for obtaining such a plasmid for expression of CPBII cDNA, unicellular microorganisms such as bacteria and yeast, notably, *E. coli, B. subtilis, S. cerevisiae* or Streptomyces are preferred. Cultured cells of mammals can also be used for this purpose. When E. coli is chosen as a host, various variants of the K12 strain of E. coli, for example, HB101, C600K, JM101, JM105, JM109, x1776, MV1304 and the like may be used.

DNA used as a vector may preferably be plasmid. Where E. coli is used as a host by way of example, plasmid DNA has a DNA sequence required for the multiplication of the plasmide in cells of E. coli, for example, the DNA sequence of the starting region of replication of ColEL plasmid and also has another DNA sequence capable of serving as a promoter and transcription terminator. It is more preferable that the plasmid DNA contains a gene capable of acting as a selective marker in a transformant of E. coli. Illustrative example of the promoter may include promotors such as λPL, lac, trp, tac and lpp. As an exemplary transcription terminator, may be mentioned rrnB ribosomal RNA transcription terminator of the like. As selective marker genes, may be mentioned ampicillin-resistant genes, kanamycin-resistant genes, tetracycline-resistant genes, chloramphenicol-resistant genes and so on. These genes may be used either singly or in combination.

The incorporation of a DNA having a nucleotide sequence capable of coding the amino acid sequence of the polypeptide of this invention, namely, the DNA fragment of this invention, into the above-described vector DNA may be effected by cleaving the DNA with a suitable restriction endonuclease and after adding a suitable linker if needed, joining the resultant DNA fragment with a vector DNA which has been cleaved with a suitable restriction endonuclease. Examples of the restriction endonuclease include EcoR I, Sph I, Pst I, Hind III, BamH I, Xho I, Xba I, Ban III, Sma I and Nco I. Nucleic acid-modifying enzymes can also be used, which include exonuclease III, Bal 31, S1 nuclease, exonuclease VII, mung bean nuclease and DNA polymelase I. Usable linkers include EcoR I linker, Sma I linker, Nco I linker, BamH I linker, Xho I linker, Hind III linker, Pst I linker, Sph I linker and Xba I linker.

Introduction of the resultant plasmid for expression of CPBII cDNA into host cells by the complete cell method, protoplasts method, calcium phosphate precipitation method, electroporation method or the like permits production of a transformant which has ability to produce the polypeptide of this invention efficiently.

The polypeptide of this invention can be produced by culturing the resultant transformant and the extracting and isolating the polypeptide from the thus-cultured cells and/or the resulting culture.

Upon culture of the transformant, various natural and synthetic culture media may be employed. The meduim may desirably contain carbon sources such as sugar, alcohol or organic acid salt; nitrogen sources such as protein mixture, amino acids or ammonium salt; and inorganic salts. It is also desired to add vitamins and an antibiotic corresponding to the associated selective marker gene. If the plasmid allows to control the expression, it is necessary to perform a procedure in the course of culturing so as to induce the expression. After the culture, centrifugation is conducted to separate the resultant culture broth into culture and cultured cells. Where the polypeptide of this invention accumulates in the cells cultured, it is necesary to disrupt or fractrure the cells by freeze thawing, ultrasonic processing, Frence press, enzyme treatment, homogenizer or the like and then to solubilize the polypeptide of this invention, for example, with EDTA, surfactant, urea, guanidine hydrochloride or the like.

The resultant culture or cultured cell extract, which contains the polypeptide of this invention, is subjected to chromatography on one of various columns, so that the polypeptide of this invention can be obtained in a purified form. As a column chromatography, ion-exchange chromatography, affinity chromatography and gel chromatography may be applied either singly or in combination.

The thus-obtained polypeptide of this invention has the following properties.

(1) Amino acid sequence:

The amino acid sequence of the polypeptide of this invention, which is translated into from the nucleotide sequence of the DNA fragment of this invention is shown in FIG. 1.

(2) Molecular weight:

75,700 (calculated from the amino acid sequence). 73,000±2,000 (ADS-polyacrylamide gel electrophoresis, reduced state)

As a dosage form upon using the polypeptide of this invention as an active ingredient for an anticoagulant, an injection may be mentioned. As the injection, it is preferable to form the polypeptide lyophilized powder so that whenever needed, the polyopeptide may be dissolved in distilled water for injection, physiological saline or the like for administration. The suitable route of its administration is intravenous.

Although the dose of the polypeptide varies depending on the severity of disease, the body weight of each patient, etc., it is generally preferable to administer it at 10μg–10 mg/kg.day. The polypeptide of this invention does not develop any appreciable abnormality and is safe so long as it is administered within the above dose range.

Since the polypeptide of this invention exhibits strong anticoagulant activites, an anticoagulant containing it as an active ingredient is useful for the prevention and treatment of various diseases caused by exasperation of coagulative activities, for example, thrombosis, DIC (disseminated intravascular coagulation) and the like in the brain, heart and peripheral blood vessels, such as cerebral infarction and myocardial infraction. In addition, the polypeptide of this invention has properties similar to those of the placental coagulation inhibitor (CPBII) derived from the human placenta. It is hence a safe substance having no anitgenecity against men. In spite of the fact the CPBII is useful as an anticoagulant, it is accompanied by the drawback that it cannot be produced in any large amount due to difficulties in the availability of human placentae. In contrast, the polypeptide of this invention can be produced in a large amount and at a low price.

EXAMPLES

The present invention will hereinafter be described with reference to the following Referential Examples and Examples.

referential Example 1: Preparation of Anti-CPBII Monoclonal Antibody (1) Purfication of antigen (CPBII):

(a) Five human placentae (about 2,500 g) were minced subsequent to removal of membranes and the like and thorough washing with physiological saline. The thus-minced placentae were ground in a Waring blender and then added with 2 liters of 50 mM tris-hydrochloric acid buffer (pH 7.4), followed by further comminution with a "Polytron". The resulting homogenate was subjected to centrifugal separation at 7,000 r.p.m. for 15 minutes to collect a sediment. Two liters of 50 mM tris-hydrochloric acid buffer (pH 7.4) was added again to the thus-collected sediment, and the resluting mixture was homogenized with the "Polytron" and then subjected to centrifugal separation at 7,000 r.p.m. for 15 minutes to obtain a washed sediment. The above procedure was repeated several times until blood components were removed to obtain about 900 g of washed sediment finally.

(b) About 2 liters of 50 mM tris-hydrocholoric acid buffer (pH 7.4) containing 50 mM of EDTA was added to 900 g of the sediment obtained in the above procedure (a), followed by homogenization in the Waring blender. The resulting homogenate was agitated overnight at 4° C., followed by centrifugal separation at 7,000 r.p.m. for 15 minutes to obtain 2 liters of extract.

(c) Solid ammonium sulfate was added to the extract obtained in the above procedure (b) to 35% of its saturated concentration. After allowing the resultant mixture to stand at 4° C. for 30 minutes to several hours, it was centrifuged at 7,000 r.p.m. for 15 minutes to collect a supernatant. Ammonium sulfate was added further to the supernatant to 85% of its saturated concentration. The resultant mixture was allowed to stand at 4° C. for 2 hours, followed by centrifugation at 7,000 r.p.m. for 15 minutes to collect a sediment. The thus-obtained sediment was dissolved in a small amount of 20 mM tris-hydrochloric acid buffer and thoroughly dialyzed overnight at 4° C. against same buffer. Precipitates formed during the dialysis were removed by centrifugation at 7,000 r.p.m. for 15 minutes to obtain 390 ml of dialyzate.

(d) The thus-obtained dialyzate was adsorbed on a DEAE-Toyopearl column ($\phi 5.5 \times 19$ cm) which had been equilibrated with 20 mM tris-hydrochloric acid buffer (pH 7.4) and washed thoroughly with the same buffer. Using 4-liter portions of the same buffer which portions contained 0 to 0.3M of sodium chloride respectively, elution was then performed at a rate of 20 ml per fraction in accordance with the linear concentration gradient method. Active fractions were eleuted around a sodium chloride concentration of approximately 0.2M, thereby obtaining 200 ml of active fractions.

(e) The resultant active factions were concentrated through a "DIAFLOW Membrane Filter YM-10".

The concentrate was subjected to gel filtration using a "Sephadex G-100" column ($\phi 4.5 \times 75$ cm) and eluted at a rate of 8 ml per fraction with a physiological saline. Active fraction Nos. 70–82 were collected and concentrated by ultrafiltration to obtain 14 ml of CPBII (protein weight: 59.3 mg, Lowry method).

(2) Preparation of immunized spleen cells:

The above-purified CPBII (100 µg) was emulsified in Freund complete adjuvant and administered intraperitoneally to BALB/c mice.

CPBII (50 µg/administration) mixed with adjuvant was thereafter administered twice at an interval of 2 weeks and finally, 50 µg of CPBII was administered solely to complete the immunization.

Three days later, the mice were sacrificed. After taking out their spleens and chopping same, they were filtered through a 100-mesh nylon mesh to obtain isolated spleen cells.

(3) Preparation of hybridoma:

A hypotonic solution (155 mM ammonium chloride) was added to the thus-obtained immunized spleen cells to subject red blood cells to hemolysis. The cells were then washed with Isocove's modified Dulbecco's medium (IMDM). On the other hand, mouse myeloma cells PAI were also washed twice with IMDM. Both cells were counted. The spleen cells and PAI cells were combined together at a ratio of 5:1, followed by centrifugation. The supernatant was decanted out, and a buffer solution for cell fusion (mannitol 0.25M, $CaCl_2$ 0.1 mM, $MgCl_2$ 0.1 mM, tris-HCl 0.2 mM, pH 7.2) was added to the resultant cell sediment, followed by agitation and centrifugation. This operation was repeated twice. The buffer solution for cell fusion was added to the cell sediment so that the cell density was adjusted to $4 \times 10^7$/ml. An amount of 100–200 µl was taken therefrom and dropped between the electrodes of a cell fusion apparatus (Model SSH-1, manufactured by Shimazu Seisakusho K.K.). 1 MHz, 40 V power was supplied for 10 seconds followed by electric pulses of 300 V, 1/60 sec. several times. After leaving as is for 5 minutes, cells between the electrodes were washed with IMDM and placed in a centrifugal tube for centrifugation at 1,000 r.p.m. for 8 minutes.

The resulting sediment was suspended in IMDM which had been added with 10% of fetal calf serum (FCS). The suspension was centrifuged again and the resultant supernatant was decanted out.

The thus-obtained sediment was suspended again so as to have a cell density of $4 \times 10^6$/ml in 10% FCS-added IMDM in which $10^{-4}$M of hypoxanthine, $4 \times 10^{-7}$M of aminopterin and $1.6 \times 10^{-5}$M of thymidine (HAT—) had been added in advance. The resultant suspension was poured in 100-µl portions into the individual wells of a 96-well microtiter plate. Each well was added with 50 µl of the medium every third to fourth day. Growth of cells was observed.

It was confirmed that hybridomas were only allowed to grow owing to the selective action of HAT.

(4) Screening of antibody-secreting hydbridoma:

The culture in a well, in which hybridomas had grown, was collected and a test was performed by enzyme immunoassay to determine if CPBII-antibody secreting hybridomas were contained there. First of all, CPBII was poured at a rate of 0.1 µg/100 µl/well into each well of a 96-well microtiter plate ("Immunoplate I", product of NUNC Company). The microtiter plate was left over at 25° C. for 18 hours so as to adsorb CPBII. Thereafter, a culture as a sample was poured at a rate of 100 µl/well to react at 25° C. for 2 hours. After washing the culture three times with phosphate-buffered saline containing 0.05% of "Tween 20" (PBS-Tween), horse radish peroxidase conjugated goat anti-mouse IgG (product of KPL Laboratories, Inc.) was added at a rate of 100 µl/well and two hours later, the culture was washed three times with PBS-Tween. Each well was then added with 0.1M citric acid-sodium hydroxide buffer (pH 4.0) containing 0.001% of hydrogen peroxide solution and 0.4 mg/ml of orthophenylenediamine (product of Sigma Chemical Company). The color development was stopped by adding 50 µl of 4.5M sulfuric acid and the absorbance of each well was measured at a wavelength of 492 nm.

Since development of color was observed only in wells where an antibody to CPBII existed in the sample, cells were collected from the wells which were stained.

(5) Cloning of hybridomas which secrete a monoclonal antibody specific to CPBII:

Abdominal cells collected by injecting IMDM into the abdominal cavity of a mouse were used as feeder cells.

The abdominal cells suspended at 1×10⁵ cells/ml in 10% FCS-added IMDM were poured in 100-μl portions into the individual wells of a 96-well microtiter plate. On the following day, antibody-secreting hybridomas were prepared at a concentration of 5 cells/ml and poured in 100-μl portions into the individual wells. Every third day, the culture medium was replaced by a fresh supply of the same medium, and culture supernatants were successively sampled out from wells in which hybridomas had grown to an appropriate volume. Confirmation of the secretion of the antibody was conducted by the same method as that described above. The cultures of positive wells were cloned again to obtain hydribomas secreting an anti-CPBII monoclonal antibody. Four types of hybridomas were obtained. They were named CPBII-H29, CPBII-H76, CPBII-H311 and CPBII-H511 in accordance with the types of the anti-CPBII monoclonal antibodies which they secreted respectively.

Referential Example 2: Preparation of Anti-CPBII Monoclonal Antibody

Seven week-old or still older BALB/c mice were intraperitoneally administered with 0.5 ml of pristane (product of Aldrich Chemical Co., Inc.). About one week later, the mice were intraperitoneally inoculated with the above-obtained hybridomas at a rate of 1×10⁶ cells/mouse. About 10 days later, ascitic fluid was collected from the abdominal cavities of the mice. The fuild was centrifuged at 3,000 rpm for 10 minutes to collect a supernatant. Ammonium sulfate was added to 5 ml of the supernatant until the final concentration of ammonium sulfate reached 50% saturation. The resultant mixture was stirred for 60 minutes at 4° C. The mixture was then centrifuged at 10,000 rpm for 20 minutes, and the resultant sediment was dissolved in a 0.1M tris-hydrochloric acid buffer (pH 8) and thereafter dialyzed against the same buffer. The resulting dialyzate was subjected to chromatography on a column packed with "Protein A Sepharose CL-4B" (product of Pharmacia AB) which had been equilibrated with the same buffer added with an equivalent amount of 1.5M glycine-3M sodium chloride buffer (pH 8.9).

The elution of the monoclonal antibody was conducted with 0.1M citric acid buffer (pH 4), whereby the anti-CPBII monoclonal antibody was obtained. When CPBII-H29 was used, 22.2 mg of CPBII-A29 was obtained. 7.8 mg of CPBII-A76 from CPBII-H76, 16 mg of CPBII-A311 from CPBII-H311, and 29 mg of CPBII-A511 from CPBII-H511.

Referential Example 3: Purification of CPBII by Immunoadsorption Chromatography (1) Binding of anti CPBII monoclonal antibody to a carrier:

Cyanogen bromide-activated Sepharose 4B (0.4 g) was washed with 1 mM hydrochloric acid and 0.1 mM sodium bicarbonate-0.5M sodium chloride buffer (pH 8.3) in this order to prepare a suspension of cyanogen bromide-activated Sephalose 4B in a coupling buffer (1.5 ml).

To the suspension was added a coupling buffer (1 ml) containing 2 mg of purified monoclonal antibody CPBII-A76, stirred for 2 hours at room temperature followed by dehydration through a glass filter. 10 ml of 0.1M tris-hydrochloric acid buffer (pH 8.0) was added and stirred for 2 hours to block the remaining active sites.

The obtained antibody-bound Sepharose 4B was washed with 0.1M tris-hydrochloric acid-0.5M sodium hydrochloride buffer (pH 8.3) and 0.1M acetic acid-0.5M sodium chloride buffer (pH 4.0) alternately three times and equilibrated with 0.1M tris-hydrochloric acid buffer (pH 7.4) to obtain an antibody column #76.

(2) Purification of CPBII by use of antibody column #76:

The antibody column #76 prepared in (1) above was added with a crude CPBII solution obtained in Referential Example 1-(1)-(b), and washed well with the same buffer used for equilibration.

The elution of CPBII can be carried out according to either method of (1) using 0.1M acetic acid-0.5M sodium chloride buffer (pH 3.5) or (2) using 0.2M glycine-hydrochloric acid buffer (pH 2.3).

CPBII was not recognized in a non-adsorped fraction but was isolated from the elution fraction at a recovery ratio over 80%.

The CPBII was subjected to measurement as described in Referential Example 4.

Referential Example 4: Measurement of CPBII by Use of Anti CPBII Monoclonal Antibody According to the method proposed by S. Yoshitake et al. [J. Biochem. 92, 1413–1424, 1982], horse radish peroxidase (hereinafter referred to as HRP) was bound to anti CPBII monoclonal antibody. Using this HRP-conjugated anti CPBII monoclonal antibody, CPBII was measured according to an ELISA method. To each well of 96-well flat bottom microtiter plate was placed 100 μl of monoclonal antibody dissolved in 0.05M sodium carbonate (pH 9.6) for coating over 2 hours at 25° C. After being washed with PBS-Tween, the well was added with 100 μl of a sample solution in 0.1M Tris HCl buffer (pH 7.4) containing 25 mM EDTA, and 0.05% Tween 20, followed by an overnight reaction at 25° C., washed with PBS-Tween. 100 μl of the HRP-conjugated monoclonal antibody solution diluted with PBS-Tween was added for reaction over 2 hours at 25° C. After washing with PBS-Tween, 100 μl of substrate solution (0.1M citric acid phosphoric acid buffer solution of 0.4 mg/ml orthophenylenediamine and 0.01% hydrogen peroxide; pH 5.0) was added for reaction over 30 minutes at 25° C. 50 μl of 4.5M sulfuric acid was added to terminate the reaction, and absorbance at 492 nm was measured. It was revealed that 1 to 100 ng/ml CPBII could be detected when CPBII-A29 was used as a monoclonal antibody for coating and CPBII-A76, CPBII-A311 and CPBII-A511 were used as a monoclonal antibody to be conjugated; or CPBII-A511 was used as the former and CPBII-A29, CPBII-A76 were used as the latter.

When CPBII-A29 was used as a monoclonal antibody for coating and CPBII-A511 was used as a monoclonal antibody to be conjugated, a very high sensitivity was obtained and the calibration curve exhibited a good linearity.

EXAMPLE 1

Preparation of Anti-CPBII Polyclonal Antibody (1) Preparation of rabbit antiserum:

0.8 mg of CPBII obtained in Referential Example 1 was emulsified in Freund complete adjuvant and administered to a foot pad of a rabbit (white local breed, male). At an interval of 2 weeks, 0.8 mg emulsion of CPBII and adjuvant was administered twice, and then the same amount of CPBII emulsified in Freund incomplete adjuvant was subcutaneously administered to complete the immunity. Whole blood was collected from the rabbit thus immunized to obtain 80 ml of serum. The antibody titer of the serum was measured according to an Ouchterlony method using CPBII as an antigen, which revealed a titer of 8-fold.

(2) Purification of antibody:

2.5 ml of human albumin solution (4 mg/ml) was added to 80 ml of antiserum obtained in (1) above, allowed to stand for two hours at room temperature and centrifugally separated for 10 minutes at 14,000 rpm for absorption of anti-human albumin antibody. To 78 ml of the resultant supernatant was added 78 ml of PBS (0.29% disodium hydrogen phosphate, 0.02% potassium dihydrogen phosphate, 0.8% sodium chloride, 0.02% potassium chloride) and 156 ml saturated ammonium sulfate solution. After being allowed to stand overnight at 4° C., centrifugation was carried out at 10,000 rpm for 10 minutes to obtain a sediment. The thus-obtained sediment was dissolved in PBS and dialyzed against sufficient amount of PBS. The dialyzate was centrifugally separated at 10,000 rpm for 10 minutes and was adsorbed on a Protein A-Cellulofine column which was equilibrated with PBS. PBS was used for washing and 0.1M glycine-hydochloric acid buffer (pH 2.7) containing 0.15M sodium chloride was used for elution. pH was adjusted to neutral with tris solution. The resultant solution was passed through a Sepharose column on which Calphobindin (Maki et al, Sanpu Ketsueki 12(1), 41–48, 1988) was immobilized. The passed liquid was added with lipocortin fraction prepared from the human placenta according to Huang et al., Cell, vol 46, p 191, 1986 and allowed to stand overnight at 4° C., centrifugally separated at 15,000 rpm for 10 minutes to have anti-lipocortin antibody absorbed. The centrifugal supernatant was adsorbed on Sepharose column on which CPBII was immobilized in advance, washed with PBS, eluted with 0.1M glycine-hydrochloric acid buffer (pH 2.7) containing 0.15M sodium chloride. pH was adjusted to neutral with tris solution. The elute was dialyzed against distilled water, then freeze-dried to obtain 10.3 mg of purified anti CPBII polyclonal antibody.

EXAMPLE 2

Cloning of CPBII cDNA (1) Screening of the human placental cDNA library:

(a) cDNA library:

The human placental cDNA library was a product of Clontech Laboratories, Inc. cDNA, which had been prepared from human palcental mRNA of 1.8 kb on average by using reverse transcriptase, was coupled to the EcoR I site of λgtll phage by way of an EcoR I linker. The library composed of $1.0 \times 10^5$ independent clones of recombinant λgtll phage.

(b) Host E. coli cells Y1090 (ATCC 37197) were streaked on an LB agar plate (10 g Bacto-tryptone, 5 g Bacto-yeast extract, 5 g sodium chloride, 2 g maltose, 15 g agar, 1 liter distilled water; pH 7.5) which contained ampicillin (100 μg/ml), followed by overnight culture at 37° C. A single colony thus occurred was transplanted to an LB medium (10 g Bacto-tryptone, 5 g Bacto-yeast extract, 5 g sodium chloride, 2 g maltose, 1 liter distilled water; pH 7.5) which contained ampicillin (100 μg/ml), followed by overnight shaking culture at 37° C.

(c) Infection of the phage library:

An overnight culture (0.2 ml) of host E. coli Y1090 cells was mixed with 0.1 ml of the phage library which had been prepared to $5.5 \times 10^5$ pfu/ml with a λ diluent (10 mM tris-HCl buffer, 10 mM magnesium chloride; pH 7.5). The resultant mixture was stood for 20 minutes at room temperature to have the phage adsorbed on the host cells. After addition and mixing of 2.5 ml of an LB top layer agar medium (10 g Bacto-tryptone, 5 g Bacto-yeast extract, 5 g sodium chloride, 2 g maltose, 7.2 g agar, 1 liter distilled water; pH 7.5) which had been maintained warm at 45° C., the resultant mixture was spread on an LB agar plate having a diameter of 9 cm and was then cultured at 42° C. for 3 hours and a half.

(d) Transfer to a nitrocellulose filter:

After the sterilized nitrocellulose filter was saturated with 10 mM of isopropyl-β-D-thiogalactopyranodise (IPTG), it was dried. The dried filter was then applied over the LB agar plate which had been cultured at 42° C. for 3 hours and a half and contained λgtll phage plaques occured. After culturing at 37° C. for additional 3 hours and a half, the filter was peeled off. The plate with the phage plaque occurred was stored at 4° C. After washing the filter with TBST (100 mM tris-HCl buffer, 150 mM sodium chloride, 0.05% "Tween 20"; pH 8.0), the filter was subjected to blocking at room temperature for 30 minutes with 1% bovine serum albumin/TBST.

(e) Binding of a primary antibody:

The filter was placed in a solution of the primary antibody and was reacted at room temperature for 60 minutes under gentle shaking. As the primary antibody, the anti-CPBII rabbit polyclonal antibody (obtained in Referential Example 1.) dissolved in the TBST was employed after allowing the liquid mixture to stand at room temperature for 30 minutes and absorbing foreign antibodies. As an anti-CPBII rabbit polyclonal antibody liquid mixture, was employed that containing 0.1 μg/ml of anti-CPBII rabbit polyclonal antibody, 1 mg/ml of bovine serum albumin and 0.25 μg/ml of an E. coli extract (product of Promega Corporation).

After the reaction with the primary antibody, the filter was washed three times, for 10 minutes each, with TBST.

(f) Binding of a secondary antibody:

The filter was then transferred into a solution of the secondary antibody and reacted at room temperature for 30 minutes under gentle stirring. As the secondary antibody was used that obtained by diluting an alkaline phosphatase-conjugated anti-rabbit IgG (H+L) (product of Promega Corporation) to a concentration of 1/7,500 of its original concentration with TBST.

The filter was then washed three times, for 10 minutes each, with TBST, followed by washing once with an AP buffer (100 mM tris-HCl buffer, 100 mM sodium chloride, 5 mM magnesium chloride; pH 9.5).

(g) Color development:

The filter was immersed in a color development substrate solution which had been obtained by mixing 33 μl of a nitroblue tetrazolium solution (50 mg/ml) and 66 μl of a solution of 5-bromo-4-chloro-3-indolyl phosphate (50 mg/ml).

After allowing a stain to develop at room temperature for 1 hour, the filter was transferred into a reaction terminating solution (20 mM tris-HCl buffer, 5 mM sodium ethylenediamine tetraacetate; pH 8.0) so as to terminate the color development.

(h) Preparation and purification of positive plaques:

Plaques corresponding to positive spots where color development was observed were collected together with the agar medium and were then transferred into a 0.1 ml of a TMG buffer (10 mM tris-HCl buffer, 10 mM magnesium chloride, 100 μg/ml gelatin; pH 7.4). Two drops of chloroform were added, followed by centrifugation at 4° C. and 4,000 rpm for 15 minutes. One drop of chloroform was then added to the resultant supernatant and the thus-prepared mixture was stored at 4° C.

The above-described screening was conducted on about $1 \times 10^6$ phage plaques. As a result, 26 positive plaques were obtained.

With respect to four plaques which showed strong color development, their phage solutions were separately diluted to a suitable extent and then subjected to screening twice to obtain purified phages, C-1, C-4, C-5 and C-6.

(2) Preparation of recombinant phage DNA:

Host *E. coli* cells Y1088 (ATCC 337195) were infected with the thus-obtained 4 strains of recombinant phages, and the phages were induced to occur at 42° C. Following a preparation method of λ phage [Bernard Perbal, PREPARATION OF λ PHAGE DNA in A PRACTICAL GUIDE TO MOLECULAR CLONING, pp 175-184, A Wiley-Interscience Publication (1984), New York, U.S.A.], a small-volume preparation and a large-volume preparation, both, by the plate method and a large-volume preparation by a liquid culturing method were conducted successively to obtain $10^9$ pfu/ml of recombinant phages.

In accordance with a λDNA preparation process [Bernard Perbal, PURIFICATION OF λ DNA in A PRACTICAL GUIDE TO MOLECULAR CLONING, pp 184-187, A Wiley-Interscience Publication (1984), New York, U.S.A.], a phage solution which had been concentrated to $10^{11}$ pfu/ml by the polyethylene glycol precipitation method was purified by ultra-centrifugation in 2 step-concentration of glycerol [Written by Bernard perbal, translated by Shigeyasu Kobayashi: Practical Handbook of Gene Manipulation Experiments, pp 175 (1985), The Jatec Publishing Co.].

Using the purified recombinant phage, recombinant phage DNA was also prepared in accordance with the preparation method of λDNA. About 50-100 μg of DNA was obtained from 300 ml of the culture.

(3) Subcloning of cDNA:

pUC118 (product of Takara Shuzo Co., Ltd.) was used as a vector. pUC118 was cleaved with EcoR I. The four strains of recombinant λgtll phage DNAs were separately ligated with the thus-cleaved pUC118 by using a DNA ligation kit (product of Takara Shuzo Co., Ltd.).

When recombinant vectors thus obtained were separately introduced in host *E. coli* cells MV1304 (product of Takara Shuzo Co., Ltd.), recombinant vectors having a different direction of insertion and a different molucular weight, corresponding respectively to the 4 strains of the recombinant λgtll phage DNAs were obtained from the resultant transformants of the host cells MV1304. From C-1 was obtained recombinant vectors pKSI 11, pKSI 12 and pKSI 13, from C-4 was obtained pKSI 41, from C-5 was obtained pKSI 51 and pKSI 53 and from C-6 was obtained pKSI 61, pKSI 63 and pKSI 64.

Restriction endonuclease maps were prepared by cleaving the recombinant vectors by the use of various restriction endonuclease. The maps are shown in FIG. 3. CPBII cDNA contained an EcoRI site in the inserted fragment. By a subcloning operation, a subclone containing a large fragment and a subclone containing a small fragment were obtained. FIG. 4 shows pKSI 64 and pKSI 61 which were obtained from a recombinant phage C-6 containing the longest cDNA fragment. pKSI 64 and pKSI 61 had a size of 5.1 Kb and 3.7 Kb, respectively.

(4) Determination of the nucleotide sequence of CPBII cDNA:

The resultant CPBII cDNA recombinant vector was treated using various restriction endonucleases and exonuclease III-mung bean nuclease separately, so that the strand of cDNA was shortened. A short strand plasmid was then reconstructed using pUC118 as a vector. Host *E. coli* cells MV1304 were then transformed with the short-stranded plasmid thus obtained. A culture of the resultant transformant was infected with the helper phage M13K07 (product of Takara Shuzo Co., Ltd.). From phage particles thus grown, a single-stranded DNA was prepared. Its nucleotide sequence was determined by the dideoxynucleotide chain termination method (SANGER, F., NICKLEN, S. and COULSON, A. R. Proc. Nat. Acad. Sci. U.S.A. 74, 5463-5467, 1977), following the strategy shown in FIG. 3.

The nucleotide sequence of CPBII cDNA is shown in FIG. 5. It was possible to obtain cDNA of 2,425 bp which completely codes a CPBII polypeptide. An open reading frame investigation revealed that the 2016 bases starting from the 4th base GCC and ending up with the 2019th base GAC codes the CPBII polypeptide consisting of 672 amino acids.

Figure 6A:
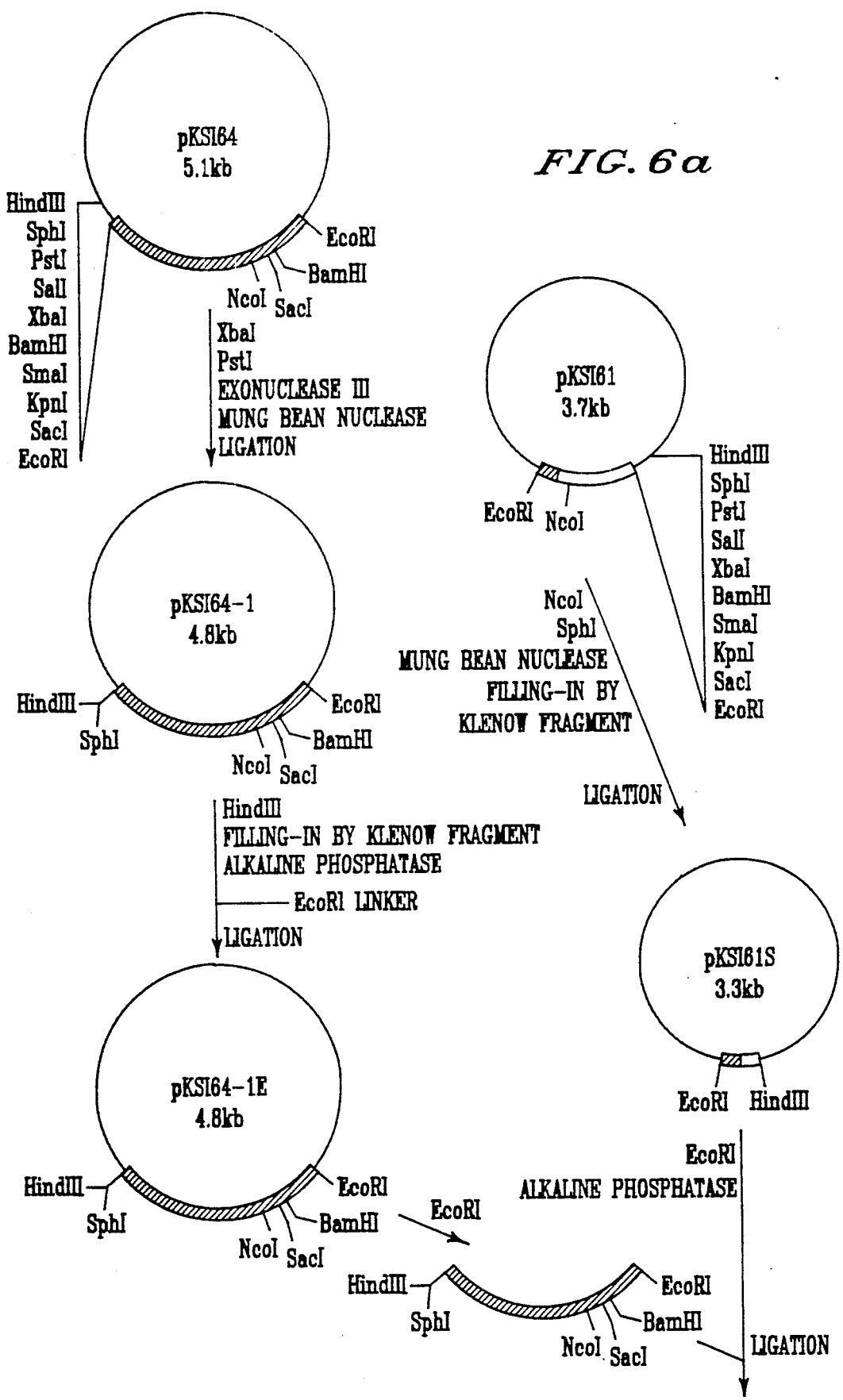
FIG. 6 shows a scheme illustrating a process for constructing a recombinant plasmid pKSI 73 of this invention.
Figure 6B:
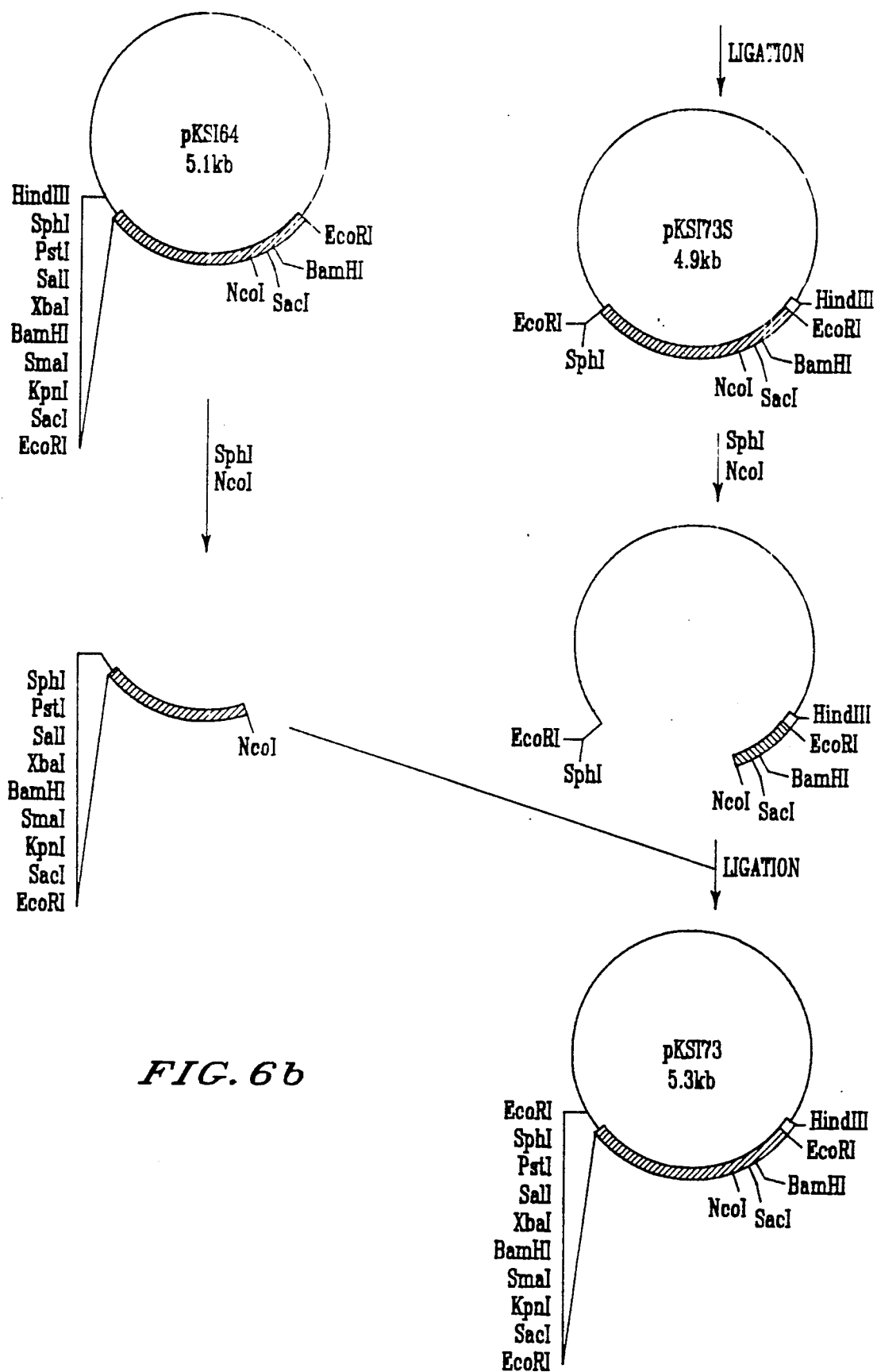

Since the cDNA which codes the polypeptide of this invention contains a single cleaveage site by EcoRI, it was cloned in two separate plasmids. In order to join the two cDNAs into a single stranded DNA, various restriction endonucleases, DNA modification enzymes and DNA linkers were used to construct a pKSI 73 which contains an open reading frame capable of coding the polypeptide of this invention from pKSI 64 and pKSI 61 as shown in FIG. 6.

*E. coli* MV1304/pKSI 73 which contains the recombinant vector, pKSI 73 has been deposited under FERM BP-1952 with Fermentation Research Institute, Agency of Industrial Science and Technology, Ministry of International Trade and Industry, Japanese Government.

EXAMPLE 3

Construction of Plasmid for Expression of CPBII cDNA and Transformation of Host Cells with the Plasmid:

(1) Selection of an expression vector:

The pKSI 73 constructed in Example 2 has a multicloning site in the upstream of the translation starting site ATG of the polypeptide of this invention. By the use of a suited restriction endonuclease, a cDNA fragment can be cut out which codes the polypeptide of this invention. Accordingly, the polypeptide of this invention is easily expressed by ligating the thus cut-out cDNA fragment with an expression vector which has a restriction endonuclease region such as EcoRI, SphI, PstI, SalI, XbaI, BamHI, SmaI, KpnI and SacI in the downstream of a strong promoter. Accordingly, it was decided to use an expression vector pKK223-3 (product of Pharmacia AB) which had the tac promoter, the strong promotor of *E. coli*, and a restriction endonuclease region of EcoRI, SmaI, BamHI, SalI, PstI and HindIII in the downstream of the ribosome-binding site.

Figure 7A:
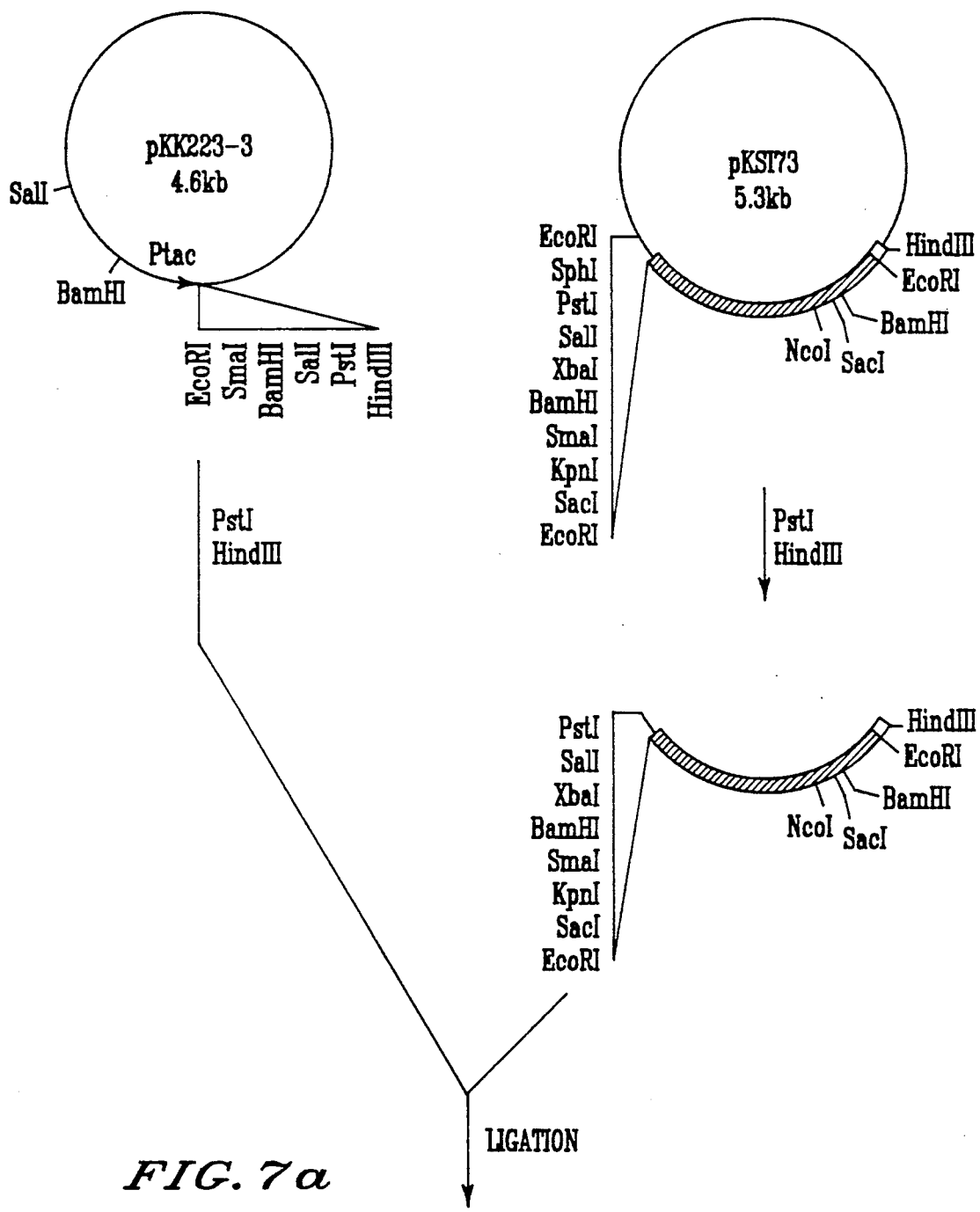
FIG. 7 shows a scheme illustrating a process for constructing a recombinant plasmid pKSI X205 for expressing the peptide of this invention.
Figure 7B:
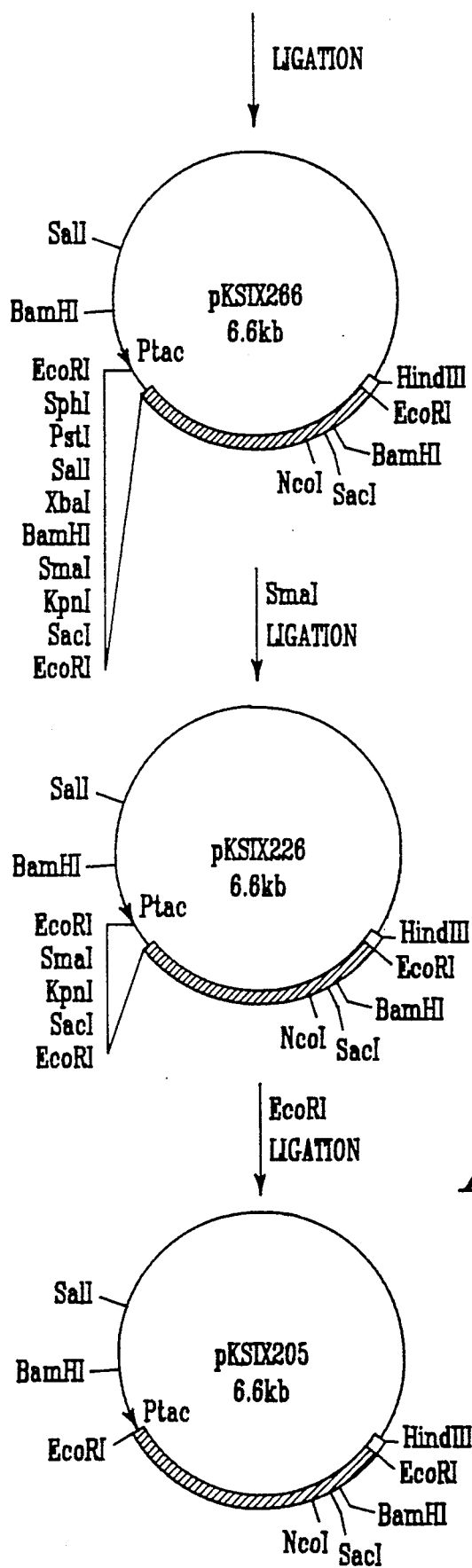

(2) Construction of a plasmid for expression of CPBII cDNA:

The plasmid pKSI 73 which had been prepared in Example 2 was cleaved with Pst I and Hind III, and ligated between PstI and HindIII of pKK223-3 by using the DNA ligation kit (product of Takara Shuzo K.K.), whereby a plasmid pKSI X266 for expression was constructed. However, since there was a distance between the ribosome-binding site and the translation starting site ATG in pKSI X266, a poor expression efficiency was expected. To overcome this, pKSI X266 was cleaved with SmaI, followed by ligation to construct pKSI X226. Thus constructed pKSI X226 was further cleaved with EcoRI, then ligated to construct pKSI X205. The procedure is shown in FIG. 7.

(3) Transformation of host cells with the plasmid for expression CPBII cDNA.

The plasmids pKSI X266, pKSI X226 and pKSI X205 which had been constructed according to the above procedure (2) was introduced into competent cells of host *E. coli* JM105 [C. Yanisch-Perron, J. Vieira and J. Messing: Improved M13 Phage cloning Vectors and Host Strains-Nucleotide Sequences of the M13mp18 and pUC19 Vectors, Gene, 33, 103–119 (1985)], which competent cells had been prepared in accordance with the method proposed by Wiestars and Simmanis [Hanahan, D.: *DNA Cloning*: A Practical Approach, Vol. 1, (D. M. Glover, ed.), pp 121, (1985) IRL Press, Oxford]. Selection of a transformant *E. coli* was effected on an LB agar plate (1% Bacto-tryptone, 0.5% Bacto-yeast extract, 1% sodium chloride, 1.5% agar) which contained 100 μg/ml of ampicillin.

Among the resultant transformant cell strains, *E. coli* JM105/pKSI X205 has been deposited under FERM BP-1953 with Fermentation Research Institute, Agency of Industrial Science and Technology, Ministry of International Trade and Industry, Japanese Government.

EXAMPLE 4

Confirmation of Expression of the Polypeptide of This Invention by the Western Blotting Technique:

*E. coli* JM 105/pKSI X205 prepared in Example 3 was cultured overnight at 37° C. on an LB agar plate which contained 100 μg/ml of ampicillin. The resultant colony was inoculated to 50-ml portions of MM medium (1.05% dipotassium hydrogen phosphate, 0.45% potassium dihydrogen phosphate, 0.1% ammonium sulfate, 0.05% sodium citrate, 0.02% magnesium sulfate, 0.2% glucose, 5 μg/ml thiamine hydrochloride), which portions were contained individually in 500-ml Erlenmeyer flasks. The transformant was cultured under shaking at 37° C. for 3 hours. Isopropyl-β-D-thiogalactopyranoside was added to a final concentration of 1 mM, followed by culture under shaking for additional 12 hours. Subsequent to collection of cells, they were suspended in 0.5 ml of TE (10 mM tris-HCl buffer, 25 mM EDTA; pH 8.0). The resultant suspension was caused to freeze in dry ice/ethanol, followed by thawing. This freezing and thawing procedure was repeated twice more, followed by centrifugal separation at 15,000 rpm for 10 minutes to obtain a supernatant of lysate. The supernatant was allowed to pass through a "Millipore" filter, so that an extract of *E. coli* JM 105/pKSI X205 was obtained.

Figure 8:
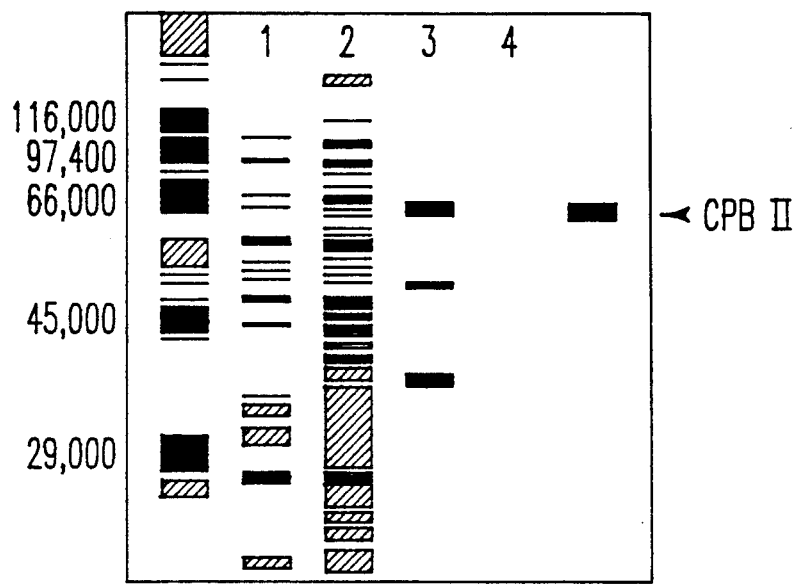
FIG. 8 is a profile of Western blotting of the polypeptide of this invention obtained from the SDS polyacrylamide gel electrophoresis.

After reducing 15 μl of the thus-obtained extract with β-mercaptoethanol, it was subjected to SDS polyacrylamide electrophoresis (10% gel). Western blotting was conducted using a mixture of anti-CPBII monoclonal antibodies CPBII-A29, CPBII-A311 and CPBII-A511 containing 1 μg/ml each and a Western blotting AP system (product of Promega Biotec Corp.). As a result, the expression of the polypeptide of this invention having a molecular weight substantially equivalent to CPBII was confirmed (FIG. 8).

EXAMPLE 5

Production of Polypeptide of This Invention (1) Culture:

The transformant *E. coli* JM105/pKSIX205 prepared in Example 3 was cultured overnight at 37° C. on an LB agar plate which contained 100 μl/ml of ampicillin. The resultant colony was inoculated to 100 ml portions of a production medium (0.7% dipotassium hydrogen phosphate, 0.2% potassium dihydrogen phosphate, 0.1% ammonium sulfate, 0.05% sodium citrate, 0.01% magnesium sulfate, 0.2% glucose, 0.5% glycerol, 0.5% casamino acid, 5 ng/ml thiamine hydrochloride, 50 μg/ml ampicillin), which portions were contained individually in 500 ml Erlenmeyer flasks. Subsequent to culturing under shaking at 200 rpm for 7 hours at 37° C., each culture was inoculated to 6 liter production medium, followed by culturing at 38° C., 500 rpm in a 10-liter jar fermenter under an air flow of 4 l/min. After culturing for 3 hours, isopropyl-β-D-thiogalactopyranoside was added to a final concentraiton of 1 mM, followed by culture for additional 15 hours.

(2) Extraction and purification:

(i) After harvesting the cells, they were suspended in 25 mM tris-HCl buffer (pH 7.5) containing 150 ml of 25 mM EDTA. The suspension was centrifugally separated to obtain washed cells. They were suspended in 150 ml of the same buffer and subjected to an ultrasonic disruption. The disrupted cells which were centrifugally separated and collected were subjected to additional twice ultrasonic disruption operations to obtain 450 ml of *E. coli* extract.

(ii) The *E. coli* extract was dialyzed against a 25 mM tris-HCl buffer (pH 7.5), and the dialyzate was caused to adsorb on a DEAE-Toyopearl column (φ2.5 × 30 cm) which had been equilibrated with the same buffer. The column was washed throughly with the same buffer, followed by another washing with the same buffer containing 0.1M sodium chloride. Using the same buffer containing 0.3M sodium chloride, elution was performed to obtain a fraction containing the peptide of this invention. DEAE fraction was caused to adsorb on antibody column #76 (5 ml) obtained in Referential Example 3. The column was washed throughly with 0.1M tris-HCl buffer (pH 8.0) containing 0.15M sodium chloride to allow elution with 0.1M acetic acid buffer (pH 3.5) containing 0.5M sodium chloride. The eluate was added with tris solution to adjust the pH to neutral, and then concentrated by the use of Milliporeimmersible CX-10, dialyzed against physiological saline to obtain a purified sample containing 1.2 mg of the polypeptide of this invention.

(3) Measurement of anticoagulant activities:

Anticoagulant activities of the peptide of this invention were measured and compared with those of placenta-derived CPBII.

(i) Prothrombin time:

50 μl of a test sample diluted with phisiological saline and 100 μl of 100-fold dilution of thromboplastin C (product of American Dade Co.) with phisiological saline were mixed and allowed to stand for 2 minutes at 37° C., to which 50 μl of human standard plasma was added. The coagulation time was then measured using a Coagulometer KC4A (product of Amelung Co.). The results are shown in Table 1.

TABLE 1

| Concentration of the sample added (μg/ml) | Coagulation Time (sec.) | |
|---|---|---|
| | Peptide of this invention | Human placenta-derived CPBII |
| 0 | 49 | 49 |
| 2.5 | 84 | 79 |
| 5.0 | 176 | 124 |
| 10.0 | 391 | 384 |

(ii) Recarcification time:

50 μl of a test sample diluted with physiological saline and 50 μl of human standard plasma were mixed and allowed to stand for 2 minutes at 37° C., to which 50 μl of a 25 mM aqueous calcium chloride solution was added. The coagulation time was then measured using Coagulometer KC4A (product of Amelung Co.). The results are shown in Table 2.

TABLE 2

| Concentration of the sample added (μg/ml) | Coagulation Time (sec.) | |
|---|---|---|
| | Peptide of this invention | Human placenta-derived CPBII |
| 0 | 260 | 260 |
| 0.4 | 588 | 578 |

EXAMPLE 6

Preparation into Dosage Form

| Polypeptide of this invention | 1 mg |
|---|---|
| Albumin | 5 mg |
| Mannitol | 25 mg |
| Sodium chloride | 1.95 mg |
| Sodium phosphate | 3.85 mg |

The above ingredients were dissolved in 2 ml of distilled water for injection. The thus-prepared solution was filled in a sterilized vial, and was frozen provisionally at −30° C. to −40° C. for 2 hours. It was thereafter subjected to primary drying at −30° C. to +20° C. and 0.05 to 0.1 Torr for 35 hours and then to secondary drying at 30° C. and 0.01 to 0.05 Torr for 5 hours, thereby producing a vial for injection.

What is claimed is:

1. A process for preventing coagulation of blood, which comprises administering to a subject in need thereof, an effective amount of anti-coagulant comprising as an active component, a substantially pure polypeptide consisting essentially of the amino acid sequence shown in FIG. 1.

2. The process according to claim 1, wherein the anticoagulant compound is administered in the form of an injection.

3. The process according to claim 1, wherein the anticoagulant compound is lyophilized and dissolved in distilled water.

4. The process according to claim 1, wherein the anticoagulant compound is lyophilized and dissolved in physiological saline.

5. The process according to claim 2, wherein the route of injection is intravaneous.

6. The process according to claim 1, wherein the amount per subject of the polypeptide ranges from 10 micrograms to 10 mg/kg per day.

7. The process according to claim 1, wherein said subject is in need of said process due to cerebral infarction or myocardial infarction.

* * * * *